US010054542B2

(12) United States Patent
Iguchi et al.

(10) Patent No.: US 10,054,542 B2
(45) Date of Patent: Aug. 21, 2018

(54) PHOTOELECTRIC SMOKE DETECTOR

(71) Applicant: Fenwal Controls of Japan, Ltd., Tokyo (JP)

(72) Inventors: Masao Iguchi, Tokyo (JP); Tadayuki Shibuya, Tokyo (JP); Kanji Numao, Tokyo (JP); Shintaro Masumoto, Tokyo (JP)

(73) Assignee: Fenwal Controls of Japan, Ltd., Tokyo (JP)

(*) Notice: Subject to any disclaimer, the term of this patent is extended or adjusted under 35 U.S.C. 154(b) by 0 days.

(21) Appl. No.: 15/190,498

(22) Filed: Jun. 23, 2016

(65) Prior Publication Data

US 2016/0305874 A1    Oct. 20, 2016

Related U.S. Application Data

(63) Continuation-in-part of application No. PCT/JP2014/003717, filed on Jul. 14, 2014.

(51) Int. Cl.
*G01N 21/53* (2006.01)
*G08B 17/107* (2006.01)
(Continued)

(52) U.S. Cl.
CPC ............ *G01N 21/53* (2013.01); *G01D 11/245* (2013.01); *G08B 17/107* (2013.01); *G08B 17/113* (2013.01)

(58) Field of Classification Search
CPC ............ G01N 21/53; G01N 2015/0693; G01N 2021/4709; G01N 30/74; G01N 15/1459;
(Continued)

(56) References Cited

U.S. PATENT DOCUMENTS 3,767,917 A * 10/1973 Lampart .............. G08B 17/113
250/384
4,396,840 A * 8/1983 Araki .................... G08B 17/11
250/381
(Continued)

FOREIGN PATENT DOCUMENTS

CN         201374114 Y     12/2009
DE      102013213721 A1     5/2014
(Continued)

OTHER PUBLICATIONS

Honeywell, "30-3003 Explosion-Proof Smoke Detector Conventional Initiating Devices", Mar. 21, 2012, pp. 1-2.
(Continued)

*Primary Examiner* — Mohamed K Amara
(74) *Attorney, Agent, or Firm* — The Webb Law Firm (57) ABSTRACT

Provided is an explosion-proofed photoelectric smoke detector capable of preventing the surrounding gas from taking fire generated by an explosion inside it and of eliminating filling spaces around a light-emitting device and a light-receiving device with resin, thereby checking explosions due to deterioration of the resin, which enables the detector to be used, with the devices exposed to gases in explosion-proof zones. The light emitting/receiving devices are arranged outside of an explosion-proof enclosure having a circuit compartment. They respectively have hollow cylinders A and B, light emitting/receiving elements, and light-guiding members A and B for transmitting emitted light and guiding received light, wherein a gap between the tube wall of each hollow cylinder and each light-guiding member and a length of each member between an opening formed in each cylinder and a light exiting/entering end thereof enable the devices to prevent fire generated inside the detector from leaking out thereof.

3 Claims, 10 Drawing Sheets

(51) Int. Cl.
*G08B 17/113* (2006.01)
*G01D 11/24* (2006.01)

(58) Field of Classification Search
CPC .. G01N 15/0205; G01D 11/245; G01D 11/30; G08B 17/113; G08B 17/107; G01K 1/08; G01K 11/32; G01K 2011/322; G01L 19/14

See application file for complete search history.

(56) References Cited

U.S. PATENT DOCUMENTS

| | | | | |
|---|---|---|---|---|
| 4,539,556 | A * | 9/1985 | Dederich | G08B 17/107 250/574 |
| 4,786,811 | A * | 11/1988 | Sasaki | G08B 17/113 250/384 |
| 4,851,819 | A * | 7/1989 | Kawai | G08B 17/107 250/574 |
| 4,897,634 | A * | 1/1990 | Sawa | G08B 17/107 174/377 |
| 5,021,677 | A * | 6/1991 | Igarashi | G08B 17/107 250/574 |
| 5,486,816 | A * | 1/1996 | Ariga | G08B 17/107 250/574 |
| 5,670,947 | A * | 9/1997 | Nagashima | G08B 17/107 250/564 |
| 6,737,977 | B2 * | 5/2004 | Nishikawa | G08B 17/107 250/506.1 |
| 6,756,905 | B2 * | 6/2004 | Rattman | G08B 17/107 250/574 |
| 6,778,091 | B2 * | 8/2004 | Qualey, III | G08B 17/107 250/574 |
| 7,697,140 | B2 * | 4/2010 | Iguchi | G01N 21/53 250/574 |
| 9,157,854 | B2 * | 10/2015 | Matsukuma | G01N 21/53 |
| 9,514,623 | B1 * | 12/2016 | Urrutia | G08B 17/107 |
| 9,652,957 | B2 * | 5/2017 | Urrutia | G08B 17/10 |
| 9,685,058 | B2 * | 6/2017 | Schmidt | G08B 29/185 |
| 2011/0068936 | A1 * | 3/2011 | Shimada | G08B 17/113 340/584 |

FOREIGN PATENT DOCUMENTS

| | | |
|---|---|---|
| FR | 2666163 A1 | 2/1992 |
| JP | 58129145 U | 9/1983 |
| JP | 638538 A | 1/1988 |
| JP | 6320050 A | 2/1988 |
| JP | 11175860 A | 7/1999 |
| JP | 2002358583 A | 12/2002 |
| JP | 3938750 A | 6/2007 |
| KR | 101269239 B1 | 5/2013 |

OTHER PUBLICATIONS

Honeywell, "30-3003 Explosion-Proof Smoke Detector Conventional Initiating Devices", Oct. 5, 2016, pp. 1-2.

* cited by examiner

PHOTOELECTRIC SMOKE DETECTOR

CROSS-REFERENCE TO RELATED APPLICATION

The present application is a continuation-in-part of PCT Application No. PCT/JP2014/003717, filed on Jul. 14, 2014, the disclosure of which is incorporated herein by reference in its entirety.

TECHNICAL FIELD

The present invention relates to a photoelectric smoke detector. More particularly, the invention relates to an explosion-proofed photoelectric smoke detector installed in an inflammable gas atmosphere, the detector capable of preventing the gas surrounding the detector from taking fire from flames of an explosion which is caused by sparks generated inside the photoelectric smoke detector.

BACKGROUND ART

Fire sensors which detect an outbreak of a fire in their surroundings by sensing heat, smoke, and/or flame generated by the fire have been known. When a fire sensor is installed in an explosion-proof zone which is filled with inflammable gas or explosive gas, an explosion due to ignition of the gas surrounding the fire sensor may be caused by sparks generated inside the fire sensor because of a failure or similar problems of electronic components. Therefore fire sensors to be installed in explosion-proof zones have to be explosion-proof so that they will not cause a far-reaching explosion in their surroundings.

Among fire sensors, smoke detectors in particular, capable of sensing smoke, are especially widely used because they are capable of detecting an outbreak of a fire in its early stage. As a kind of smoke detectors may be mentioned photoelectric smoke detectors. A photoelectric smoke detector has a light emitter and a light receiver that senses light scattered by smoke-containing air, thereby detecting smoke emission.

The photoelectric smoke detector is normally provided with an electronic circuit board to control the operations of the light emitter and the light receiver. The electronic circuit board may sometimes be caused to spark by a temporal flow of overcurrent because of a failure of electronic components, or may have an abnormally high temperature because of deterioration in insulation resistance on the face of the board. The sparks or the abnormal high temperature of the electronic circuit board may ignite inflammable gas, which may result in an explosion.

For example, a photoelectric smoke detector employing a type of protection called an intrinsic safety & intrinsically safe system is disclosed in patent document 1, or Japanese patent No. 3938750. The intrinsic safety & intrinsically safe system-type photoelectric smoke detector suppresses the magnitude of an electric current flowing on the electronic circuit board to prevent the electronic circuit board from generating such an amount of electric sparks on its surface as to ignite a surrounding inflammable gas.

In patent documents 2-4 are disclosed photoelectric smoke detectors where the light emitter and the light receiver are placed at a distance so that an explosion on the surface of the electric circuit board will not be caused.

Patent document 2, for example, discloses "a separate-type photoelectric smoke detector including a smoke detecting section to be placed in a caution zone, the smoke detecting section comprising a light-emitting element and a light-receiving lens which receives light scattered or transmitted by smoke; . . . and an electric circuit section, wherein the electric circuit section is placed at a distance from the smoke detecting section (see the claim for utility model registration of patent document 2)."

Also, patent document 3 teaches from page 3, line 17 to page 4, line 3 thereof: "The device employs the arrangement where a labyrinthine base for introducing smoke is placed at a distance from an electronic circuit including a light-emitting element, a light-receiving element, and electronic components; and the labyrinthine base and the electronic circuit are connected with optical fibers. This arrangement makes it possible to form a photoelectric smoke detector by placing only the labyrinthine base, which is not affected by high temperatures, in a high temperature room, thereby providing a smoke detector capable of detecting smoke even in a high temperature atmosphere without hindrance."

Furthermore, patent document 4 discloses from the last line in the upper right column to the fifth line in the lower left column on page 2: "The smoke detector employs an arrangement where a light emitter and light receivers for receiving direct light and scattered light are housed in a metal case of a circuit section. The emitter and the receivers are connected with a black box of the smoke sensor by optical fibers respectively. The black-box-side end of each of the optical fibers is provided with a lens for emitting or receiving light, thereby detecting smoke."

The photoelectric smoke detector using optical fibers, as disclosed in patent documents 2-4, has an arrangement where an electronic circuit board housed in an explosion-proof enclosure and the light emitting and receiving sections for detecting smoke which are wired to the electronic circuit board by means of cable glands are completely separated from each other. The resulting problem is that the detector as a whole is enlarged. Another problem is: Optical fibers made of resin are prone to attenuate smoke signals, while optical fibers made of glass are expensive because of a high price of the material.

Furthermore, the photoelectric smoke detector using optical fibers requires filling the portions of the explosion-proof enclosure to which the optical fibers are attached with resin in order to prevent penetration of explosive gas into the explosion-proof enclosure. Therefore as the filling resin deteriorates, the sealability of the explosion-proof enclosure is decreased, which may result in a high risk of explosion.

PRIOR ART DOCUMENTS

Patent Documents

Patent Document 1: Japanese Patent No. 3938750
Patent Document 2: JP S58-129145 U
Patent Document 3: JP S63-020050 U
Patent Document 4: JP S63-008538 A

SUMMARY OF THE INVENTION

Tasks to be Achieved by the Invention

The task of the present invention is to provide an explosion-proofed photoelectric smoke detector capable of preventing the surrounding gas from taking fire from an explosion inside the detector and capable of eliminating the need for filling a resin in around the light-emitting device and the light-receiving device, thereby preventing explosion caused by deterioration of the resin.

Means to Achieve the Tasks

The means for achieving the task provided by the present invention is:

(1) A photoelectric smoke detector including a light-emitting device and a light-receiving device arranged outside of an explosion-proof enclosure with a circuit compartment capable of housing an electronic circuit board, both of the light-emitting device and the light-receiving device capable of being exposed to an explosion-proof area, wherein the light-emitting device comprises a hollow cylindrical member A having a tubular wall with an inner face A, and an opening A through which an internal space A enclosed by the inner face A of the tubular wall communicates with the circuit compartment; a light-emitting element placed on a bottom of the hollow cylindrical member that borders the internal space A and faces the opening A; and a light-guiding member A for transmitting light emitted by the light-emitting element, wherein the light-receiving device comprises a hollow cylindrical member B having a tubular wall with an inner face B, and an opening B through which an internal space B enclosed by the inner face B of the tubular wall communicates with the circuit compartment; a light-receiving element placed on a bottom of the hollow cylindrical member that borders the internal space B and faces the opening B; and a light-guiding member B for guiding light to the light-receiving element, and wherein a gap between the inner face A and the light-guiding member A and a gap between the inner face B and the light-guiding member B have a width, and a portion of the light-guiding member A between the opening A and a light-exiting end of the light-guiding member A along an axis of the light-guiding member A and a portion of the light-guiding member B between the opening B and an light-entering end of the light-guiding member B along an axis of the light-guiding member B have a length, wherein the width and the length are effective to extinguish flames generated in the circuit compartment while the flames are passing through the internal space A toward the light-exiting end and through the internal space B toward the light-entering end.

(2) The photoelectric smoke detector according to item (1), wherein the photoelectric smoke detector comprises the explosion-proof enclosure; an optical device mount on which the light-emitting device and the light-receiving device are mounted so as to project from a face of the mount; and a labyrinth structure detachably layered over the mount, wherein the labyrinth structure is provided with a light-emitting device holder and a light receiving-device holder for respectively holding the light-emitting device and the light-receiving device, and provided with shields which allows gas to pass through yet prevents light from coming from the outside to the inside, on an opposite face of a contacting face of the labyrinth structure that is layered on the face of the mount.

(3) The photoelectric smoke detector according to item (2), wherein the face of the optical device mount on which the labyrinth structure is layered and the contacting face of the labyrinth structure are in a shape of a circle; the labyrinth structure has a first fixing part on the contacting face at a center of a planform of the labyrinth structure, which planform is in a shape of a circle and a second fixing part on the contacting face at a point in a radius of the circle, or the planform thereof; the optical device mount has a first positioning part in said face at a center of a planform of the optical device mount, which planform is in a shape of a circle and a second positioning part in said face at a corresponding point in a corresponding radius of the circle, or the planform thereof, wherein the first fixing part engages with the first positioning part and the second fixing part engages with the second positioning part.

(4) The photoelectric smoke detector according to any one of items (1)-(3), wherein the gap between the inner face A and the light-guiding member A and the gap between the inner face B and the light-guiding member B have a width of 0.1 mm or less, and the portion between the opening A and the light-exiting end of the light-guiding member A along the axis of the light-guiding member A and the portion between the opening B and the light-entering end of the light-guiding member B along the axis of the light-guiding member B have a length of 9.5 mm or more.

Advantages of the Invention

The photoelectric smoke detector according to the present invention has a light-emitting device and a light-receiving device wherein the above-mentioned gaps and the above-mentioned lengths between the openings A, B and the respective ends of the light-guiding members A, B are suitable for an explosion-proof construction. Thus if an explosion occurs on an electronic circuit board inside the enclosure, flames generated by the explosion are extinguished while they are passing through the gap in the light-emitting device or the light-receiving device and the explosion inside the enclosure does not leak out of it to the outside.

Also, the photoelectric smoke detector according to the present invention is explosion-proofed without requiring that gaps in the outer circumferential faces of the light-emitting device and light-receiving device be filled with resin or the like. Therefore the invention makes easier the production of the photoelectric smoke detector and the maintenance thereof, and further prevents the photoelectric smoke detector from gradually losing explosion proof due to deterioration of the resin over time.

The photoelectric smoke detector according to the present invention has a labyrinth structure capable of being detachably attached to the detector, which makes it possible to easily exchange a labyrinth structure in use with a new one if it breaks down or deteriorates. In addition, when a labyrinth structure is detached from the detector, the light-emitting device and light-receiving device is easily exposed to the outside, which provides a photoelectric smoke detector with a light emitting device and a light receiving device whose maintenance checkup is facilitated.

BRIEF DESCRIPTION OF THE DRAWINGS

FIG. 2(A) is a top plan view of a labyrinth structure, and FIG. 2(B) a bottom plan view thereof.

FIG. 3(A) is a top plan view of a sensor section 3, and FIG. 3(B) a bottom plan view of an optical device mount 31.

FIG. 9(A) is a longitudinal sectional view of a light-emitting device 35A, FIG. 9(B) a cross-sectional view taken along line (e)-(e) in FIG. 6, FIG. 9(C) a cross-sectional view of a light-guiding member A62 and its surroundings.

FIG. 10A is a longitudinal sectional view of a light-receiving device 35B, FIG. 10(B) a cross-sectional view taken along line (f)-(f) in FIG. 7, and FIG. 10(C) a cross-sectional view of a light-guiding member A72 and its surroundings.

EMBODIMENTS TO CARRY OUT THE INVENTION

We will explain the invention in detail, referring to the attached figures. The present invention is not limited to the examples shown in the figures.

As shown in FIG. 1(A), a photoelectric smoke detector 1 of the present invention has a labyrinth structure 2, a sensor section 3, an enclosure 4, and a cover 5. Although it is not shown in FIG. 1(A), the cover 5 may comprise two cover members, or an inner cover and an outer cover.

Figure 2:
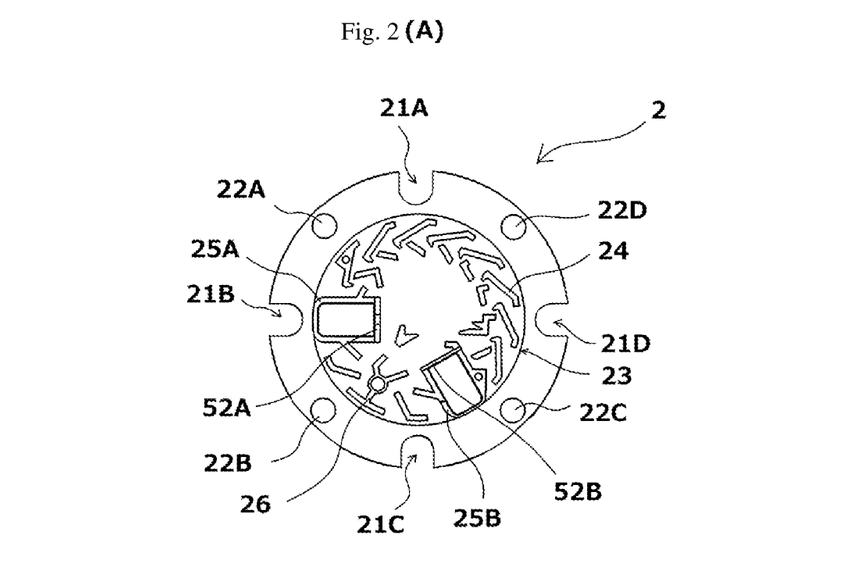

As shown in FIG. 2(A), the labyrinth structure has a planform, or a projected plan, in the shape of a general circle which has four notches 21A-21D arranged at regular intervals along a rim, or a circumference, of the general circle, four threaded holes 22A-22D for mounting the cover 5 pierced in the rim between every adjacent two notches. A detecting section 23 whose planform is in the shape of a circle is placed inside the disposition of the threaded holes 22A-22D. Within the detecting section 23 are arranged shields 24, a light-emitting device holder 25A, a light-receiving device holder 25B, and an indicator light holder 26 so as to project from the surface of the labyrinth structure 2. A plurality of shields 24 are arranged around an inner part of the detecting section 23. The shields 24 serve to prevent light from leaking from the inside to the outside and to prevent light from coming from the outside into the inside. On the other hand, an air containing smoke is allowed to pass through gaps between the shields 24 and come into the inside of the detecting section 23 from the outside.

The light-emitting device holder 25A and the light-receiving device holder 25B have a cavity inside them that is large enough to respectively hold a light-emitting device and a light-receiving device. The indicator light holder 26 has a through hole passing from the upper side of the labyrinth structure to the underside thereof, and the wall surrounding the hole is in the shape of a cylindrical tube. An indicator light, which will be described hereinafter, passes through the hole.

As shown in FIG. 2(B), the labyrinth structure 2 has underside openings 27A, 27B and 26A in the underside thereof. The underside opening 27A communicates with the cavity of the light-emitting device holder 25A in the upper side of the labyrinth structure 2, and the underside opening 27B with the cavity of the light-emitting device holder 25B in the upper side thereof. The underside opening 26A communicates with the through hole of the indicator light holder 26 on the upper side of the labyrinth structure.

Figure 1:
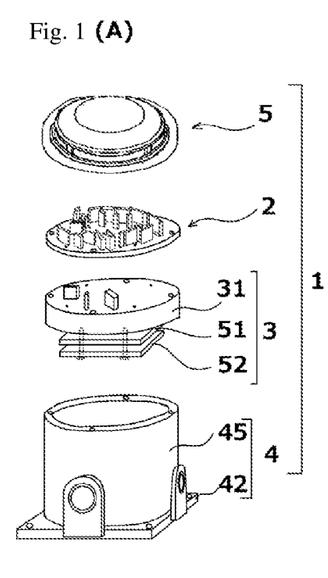
FIG. 1(A) is a schematic perspective view of a photoelectric smoke detector when it is assembled.
FIG. 1(B) is a right-side elevation of the photoelectric smoke detector after it is assembled.
Figure 3:
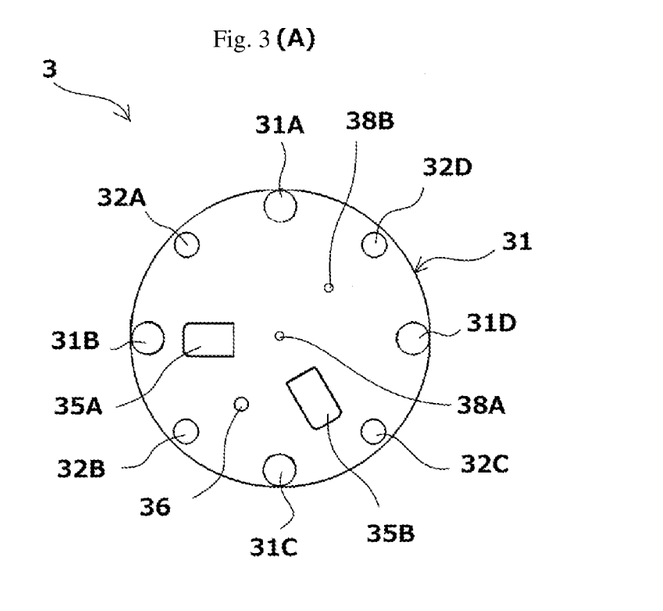

As shown in FIG. 1, on the upper side of the sensor section 3, or on the face of the sensor section 3 to be layered on the labyrinth structure 2 is formed an optical device mount 31 whose planform is in the shape of a circle. As shown in FIG. 3(A), four threaded holes 31A-31D for fixation and four threaded holes 32A-32D for mounting the cover are formed along the rim of the optical device mount 31. When the labyrinth structure 2 is layered on the sensor section 3, the threaded holes 31A-31D for fixation of the optical device mount 31 are aligned with the notches 21A-21D of the labyrinth structure 2 and the threaded holes 32A-32D for mounting the cover of the former are aligned with the threaded holes 22A-22D for mounting the cover of the latter.

Also, a light-emitting device 35A, a light-receiving device 35B, and an indicator light 36 project from the upper side of the optical device mount 31. The light-emitting device 35A and the light-receiving device 35B are so arranged that the optical axis of the former and that of the latter intersect at an angle of about 120 degrees. Light emitted by the light-emitting device 35A is scattered by smoke and some of the scattered light reaches the light-receiving device 35B. Smoke is thus detected.

The indicator light 36 may be any device as long as it is capable of emitting light signals that can be visually recognized by the user.

As shown in FIG. 3(A), a first positioning part 38A and a second positioning part 38B are formed on the upper side of the optical device mount 31. The first positioning part 38A and the second positioning part 38B engage respectively with a first fixing part 28A and a second fixing part 28B formed on the underside of the labyrinth structure 2 as shown in FIG. 2(B), or on the side of the labyrinth structure 2 to be layered on the optical device mount 31. The first and second positioning parts thus serve to prevent misalignment of the labyrinth structure 2 and the sensor section 3. For example, each of the first fixing part 28A and the second fixing part 28B may be formed as a projecting pin, and each of the first positioning part 38A and second positioning part 38B may be formed as a recess capable of receiving the pin. Insertion of the pin into the recess prevents the labyrinth structure 2 from being misaligned with the sensor section 3. The first positioning part 38A is formed at the center of the circular planform of the optical device mount 31, while the second positioning part 38B is at a point in the radius of the circle of the planform thereof. More specifically, the second positioning part 38B is at a midpoint of the segment between the center of the circle and a point on the circumference thereof. Also the first fixing part 28A is at the center of the circular planform of the labyrinth structure 2, while the second fixing part 28B is at the point of the circle of the planform thereof which corresponds to the point at which the second positioning part is formed. The engagement between the first fixing part 28A and the first positioning part 38A at the center of the respective circles prevents a sideslip of the labyrinth structure 2 or the sensor section 3 under high temperatures, which sideslip causes a misalignment of the labyrinth structure with the sensor section. Furthermore, the second fixing part 28B and the second positioning part 38B at a corresponding point in a corresponding radius of the respective circles are capable of preventing the labyrinth structure 2 or the sensor section 3 from pivoting around the center. Thus this arrangement of the fixing parts and the positioning parts is capable of effectively preventing misalignment of the labyrinth structure 2 with the sensor section 3.

On the underside of the optical device mount 31 are mounted components such as an electronic circuit board 51 and a protective plate 52 for protecting the electronic circuit board 51. The area of the planform, or projected plan, of the electronic circuit board 51 and that of the planform, or projected plan, of the protective plate 52 are smaller than the area of the planform, or projected plan, of the optical device mount 31. This is the reason that the electronic circuit board 51 and the protective plate 52 are not visible in the top plan view of FIG. 3(A).

Also, as shown in FIG. 3(B), the optical device mount 31 has underside openings 36A and 36B in the underside thereof. A wiring cable 59B connecting the light-emitting device 35A with the electronic circuit board 51 runs through the inside of the underside opening 36A, which will be described hereinafter, and a wiring cable 59C connecting the light-receiving device 35B with the electronic circuit board 51 runs through the inside of the underside opening 36B. The optical device mount 31 may have threaded holes into which circuit-mounting screws 57 for mounting a circuit board, which will be described hereinafter, are inserted in the underside thereof, although the threaded holes are not shown in the figures.

Figure 4:
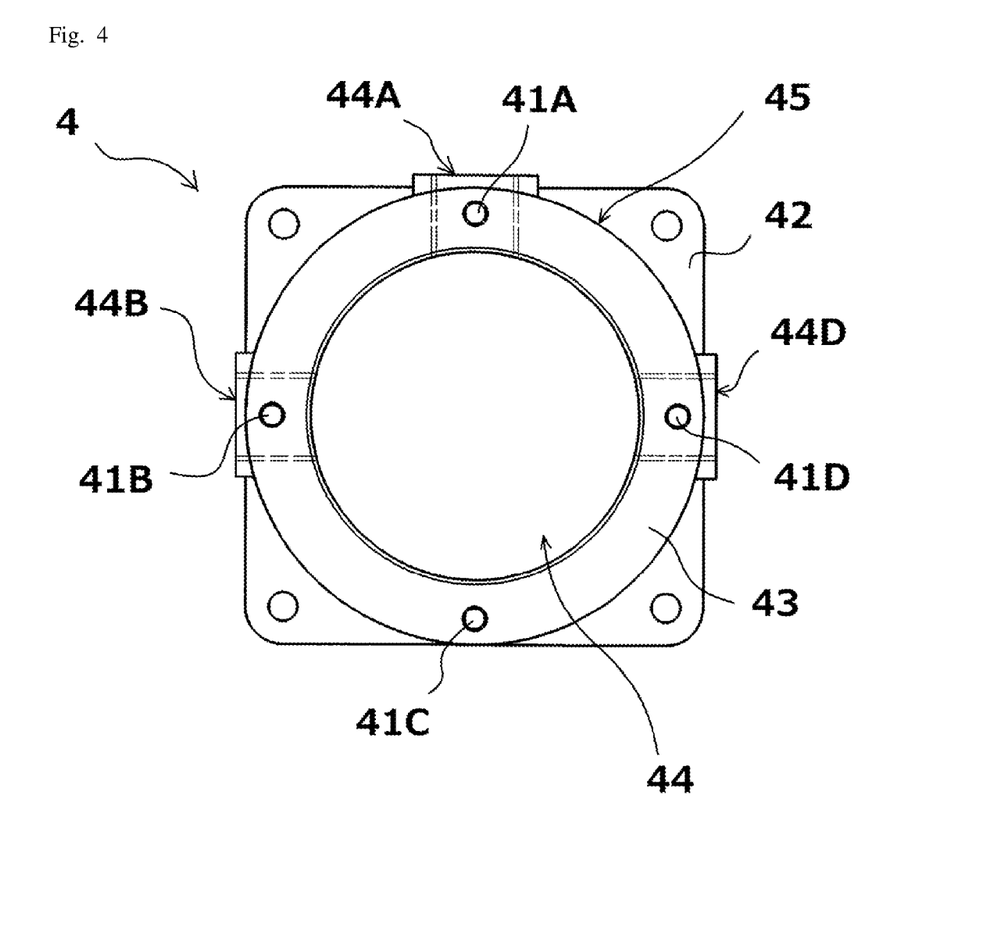
FIG. 4 is a top plan view of an enclosure.

As shown in FIG. 1(A) and FIG. 4, the enclosure 4 has a pedestal 42 whose planform is in the shape of a tetragon, and a tubular container 45 which is taller than the pedestal 42. A sealing portion 43 is provided at the top face of the tubular container 45. The sealing portion 43 is in the shape of a circle whose size is the same as that of the planform of the labyrinth structure 2 and that of the optical device mount 31. The sealing portion 43 has threaded holes 41A-41D for fixation at the positions corresponding to the positions of the threaded holes 21A-21D and those of the threaded holes 31A-31D so that the holes 41A-41D are aligned with the holes 21A-21D and the holes 31A-31D. The tubular container has a circuit compartment 44 inside the sealing portion 43 with dimensions enough to hold the electronic circuit board 51 and the protective plate 52.

Side openings through which the circuit compartment 44 communicates with the outside space may be formed in the side walls of the pedestal 42 and the tubular container 45. In the example shown in FIG. 4, three side openings 44A, 44B and 44D are formed.

In the followings, the photoelectric smoke detector 1 comprising the sections and devices which have been explained so far will be described.

Figure 5:
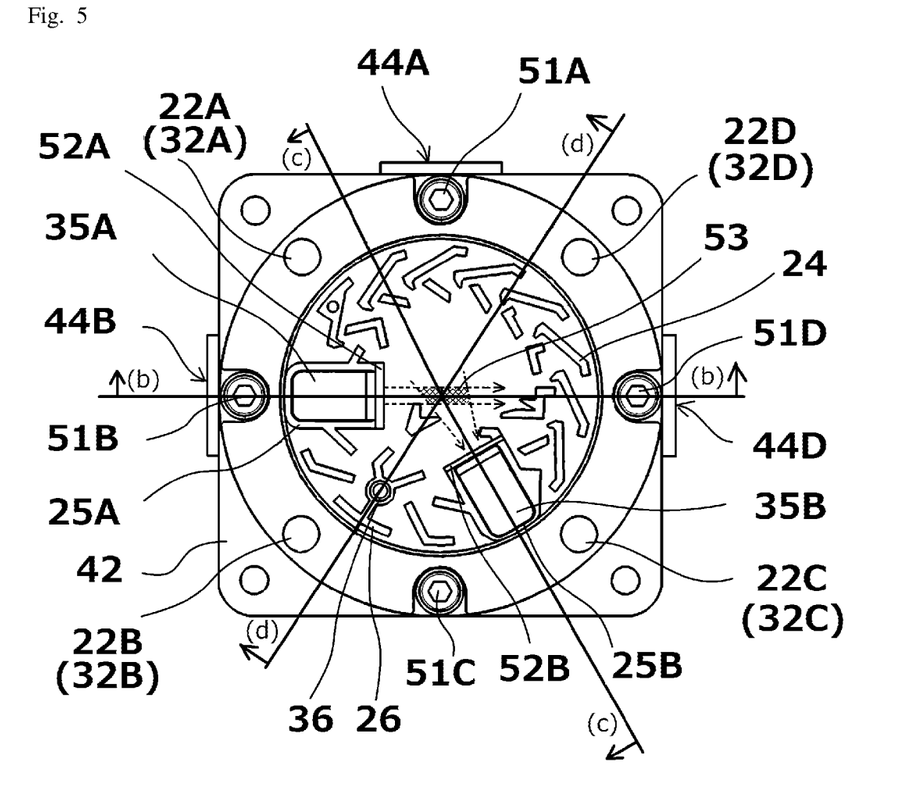
FIG. 5 is a top plan view of the photoelectric smoke detector 1, with a cover 5 being removed.

As shown in FIG. 5, the labyrinth structure 2, the sensor section 3 and the enclosure 4 are layered and fixed by inserting mounting screws 51A-51D into the notches 21A-21D of the labyrinth structure 2, the threaded holes 31A-31D for fixation of the sensor section 3, and the threaded holes 41A-41D for fixation of the enclosure 4 in this order.

Although it is not shown in FIG. 5, after the cover 5 is attached to the layered, cover-mounting screws which pass through the cover 5 are driven into the threaded holes 22A-22D and the threaded holes 32A-32D for mounting the cover, whereby the cover 5 is fixed to the layered.

When the labyrinth structure 2 is layered on the sensor section 3, the light-emitting device 35A is held by the light-emitting device holder 25A and the light-receiving device 35B by the light-receiving device holder 25B, as shown in FIG. 5. The light-exiting end of the light-emitting device 35A may be provided with a slit plate 52A so that emitted light will not diverge. On the other hand, the light-entering end of the light-receiving device 35B may be provided with a protective cover 52B to protect the device. Light emitted by the light-emitting device 35A advances through slits formed in the slit plate 52A toward a central portion of the detecting section 23. When the emitted light comes across smoke in a detecting area 53 which lies in close proximity to the central portion of the detecting section 23, the light emitted by the light-emitting device 35A is scattered. The scattered light goes through the protective cover 52B and arrives at the light-receiving device 35B. When the labyrinth structure 2 is layered on the sensor section 3, the indicator light 36 is held by the indicator light holder 26, as shown in FIG. 5.

The detecting section 23 may be provided with an insect screen around it in order that an invasion of foreign matters such as insects from the outside for the section is prevented, although the screen is not shown in FIG. 5.

When the sensor section 3 is layered on the enclosure 4, the underside of the optical device mount 31 and the sealing portion 43 of the enclosure 4 make surface contact with each other to form a sealing face 54. Also, plugs 54B and 54D are respectively inserted into the side openings 44B and 44D, which form sealing faces 55 and 56. Examples of the plugs 54B and 54D may include explosion-proof cable glands. The employment of a cable gland makes it possible to electrically connect the electronic circuit board 51 inside the photoelectric smoke detector 1 with an outside power supply, with the enclosure 4 kept explosion-proofed. The sealing surfaces 54, 55 and 56 make the enclosure 4 explosion-proof construction. Specifically, if an explosion occurs in the circuit compartment 44, flames caused by the explosion do not leak to the outside through the sealing faces. These explosion-proofed sealing faces 54, 55 and 56 may be made by conventional methods. The sealing faces 54, 55 and 56, for example, may be filled with resin. Also, the sealing faces may have such a gap as not to allow flames to leak out of the enclosure. For example, if the sealing faces 54, 55 and 56 have a gap with a width of 0.1 mm or less and a depth, or a length in the through-thickness direction, of the enclosure 4 of 9.5 mm or more, the sealing faces are able to preventing flames inside the enclosure 4 from leaking out of it.

It is not necessary to form the enclosure 4, the optical device mount 31, and the plugs 54A, 54B and 54C as separate members; they may be formed in one-piece.

The electronic circuit board 51 and the protective plate 52 are placed in the circuit compartment 44. The electronic circuit board 51 controls the light-emitting device 35A and light-receiving device 35B and the indicator light 36, and the electronic circuit board has wirings therefor. The protective plate 52 serves to mechanically reinforce the electronic circuit board 51. The electronic circuit board 51 is connected to the protective plate 52 with circuit-mounting screws 57, and both are attached to the underside of the optical device mount 31.

Figure 6:
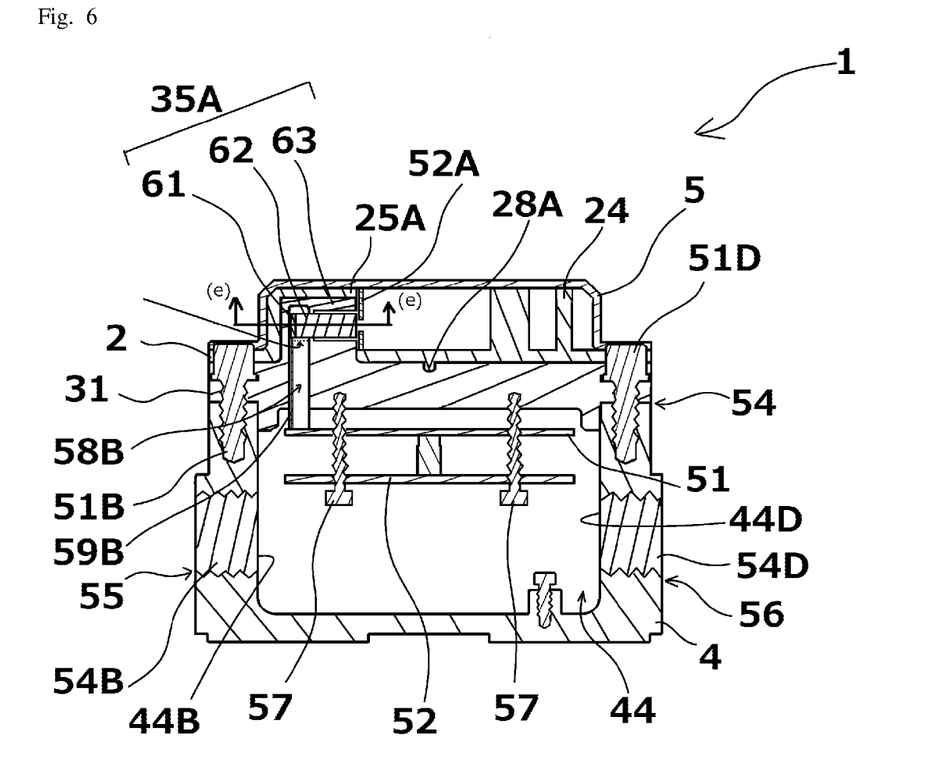
FIG. 6 is a cross-sectional view taken along line (b)-(b) in FIG. 5.

As illustrated in FIG. 6, the light-emitting device 35A is mounted on the upper side of the optical device mount 31 so that the light-emitting device projects from the mount. The light-emitting device holder 25A is formed on the labyrinth structure 2 so as to cover the outside surface of the light-emitting device 35A. The optical device mount has a cavity 58B extending through the mount to the underside thereof from the end of the light-emitting device 35A opposite the light-exiting end that emits light. The wiring cable 59B electrically connecting the light-emitting device 35A with the electronic circuit board 51 runs through the cavity 58B.

Figure 7:
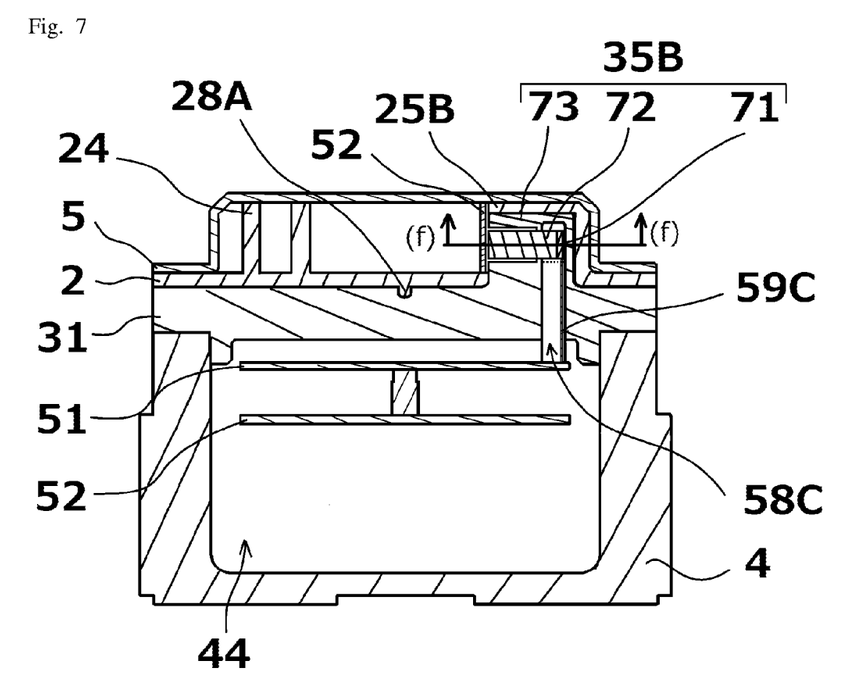
FIG. 7 is a cross-sectional view taken along line (c)-(c) in FIG. 5.

As illustrated in FIG. 7, the light-receiving device 35B is mounted on the upper side of the optical device mount 31 so that the light-receiving device projects from the mount. The light-receiving device holder 25B is formed on the labyrinth structure 2 so as to cover the outside surface of the light-receiving device 35B. The optical device mount has a cavity 58C extending through the mount to the underside thereof from the end of the light-receiving device 35B opposite the light-entering end that receives light. The wiring cable 59C electrically connecting the light-receiving device 35B with the electronic circuit board 51 runs through the cavity 58C.

Extending through the cover 5 to the outside, the indicator light 36 projects out of the photoelectric smoke detector 1, and is capable of emitting light. The user is able to check whether or not the photoelectric smoke detector 1 according to the present invention works normally by observing the indicator light from a place near the photoelectric smoke detector 1. The indicator light 36 is normally in the shape of a column and it passes through the hole of the indicator light holder 26 formed in the labyrinth structure 2. The end of the indicator light 36 opposite the light-emitting end thereof faces the circuit compartment 44, which is arranged at the underside of the optical device mount 31. Also, the indicator light is provided with the wiring cables 59D which are connected with the electric circuit board 51.

The periphery of the indicator light 36 should also be explosion proofed. Specifically, it should be designed so that flames occurring in the circuit compartment 44 will not leak along the exterior of the indicator light 36 to the outside of the photoelectric smoke detector 1. For example, the gap between the exterior circumferential face of the indicator light 36 and the inner wall of the indicator light holder 26 may be filled with a suitable material such as resin in such a manner that no space is left. Also, such a gap as to be capable of extinguishing flames generated in the circuit compartment while the flames are passing through the gap may be present between the exterior circumferential face of the indicator light 36 and surrounding walls where the indicator light holder is not present. For example, a gap with a width of 0.1 mm or less and a length along the axis of the light indicator 36 of 9.5 mm or more may serve the purpose.

As shown in FIG. 9(A), the light-emitting device 35A of the present invention has a light-emitting element 61, a light-guiding member A62, and a hollow cylindrical member A63. The light-emitting element 61 is a device capable of emitting light toward the light-guiding member A62. LED light sources, for example, may be used for the light-emitting element. The light-guiding member A62 serves to prevent the light emitted by the light-emitting element 61 from diverging and to make the light converge or advance in generally same directions. The light-guiding member A62 may be such a member that light is capable of passing through the inside thereof.

One end of the light-guiding member A62 is provided with the light-emitting element 61 and the other end thereof, or the light-exiting end 69 farther from the light-emitting element, serves to emit light to the outside. Also, as shown in FIG. 6(B), a slit plate 52A with a hole whose area is smaller than the area of each end of the light-guiding member A62 is arranged in the proximity of the light-exiting end 69 in order to make the light advance in further limited directions.

The hollow cylindrical member A63 has an internal space A66 inside it surrounded by an inner face A64 of the tubular wall, wherein the light-guiding member A62 is housed in the internal space. In the example shown in FIG. 6(C), the internal space is in the shape of a cylinder whose sectional area is larger than that of the light-guiding member A62. As a result, a gap with a width W1 is formed between the inner face A64 and the light-guiding member A62.

As illustrated in FIG. 9(C), the width of the gap is obtained as a distance from a point on the inner face A64 of the tubular wall to an outer circumferential face of the light-guiding member A62.

The hollow cylindrical member A63 is provided, at a predetermined portion thereof, with a light-guiding member-fixing part 67 for fixing the light-guiding member 62. There is no special limitation on the embodiment of the light-guiding member-fixing part 67, as long as the part is capable of fixing the light-guiding member A62. It may be a narrow circumferential projection formed on the inner face A64 so that the projection presses or squeezes the outer circumferential face of the light-guiding member A62. Also, the inner face A64 may be provided with a fixing member, such as a clamp, by means of which the light-guiding member A62 may be fixed to the inner face of the tubular wall.

As shown in FIG. 9(A), the hollow cylindrical member A63 has an opening A68 at a position closer to the bottom of the hollow cylindrical member than the light-guiding member-fixing part 67, or at a position on the light-emitting element 61 side of the light-guiding member-fixing part 67. The opening A68 is formed in a boundary between the internal space 66 and the cavity 58B that further communicates with the circuit compartment 44. The length of a portion of the light-guiding member A between the opening A68 and the light-exiting end 69 along an axis of the light-guiding member A is denoted by L1 in FIGS. 9(A) and (B). When the light-guiding member is arranged so as to wind in the internal space of the hollow cylindrical member, the length L1 is defined as a length of a winding centerline of a longitudinal section of the light-guiding member from the opening A68 to the light-exiting end 69.

As illustrated in FIGS. 10(A)-(C), the light-receiving device 35B of the present invention has a same structure as the light-emitting device 35A has, except the light-emitting element 61 is replaced with a light-receiving element 71. As a result, a gap with a width W2 is formed between the inner face B74 of the tubular wall and the light-guiding member B72. The length of a portion of the light-guiding member B between the opening B78 that communicates with the circuit compartment 44 and the light-entering end 79 is measured as L2.

The widths W1 and W2 and the lengths L1 and L2 each should be such values that the detector is capable of extinguish flames caused by an explosion in the circuit compartment 44 while the flames are passing through the internal space 66 or 76. For example, W1 and W2 each should be 0.1 mm or less, and L1 and L2 each should be 9.5 mm or more.

When the width of the gap varies according to the location on the light-guiding member, or the width W1 and/or W2 of the gap is not uniform over the length of the light-guiding member, such as an example where the central axis of the light-guiding member does not correspond to that of the internal space, the width of the gap when it is the largest should be 0.1 mm or less. More specifically, the width of the largest gap between the inner face of the tubular wall and the point on the light-guiding member, which point, among all the points on the circumference of the light-guiding member and along the axis thereof, make the gap largest, should be not more than 0.1 mm.

The operation of the photoelectric smoke detector 1 will be explained hereinafter.

Let us consider an example where the photoelectric smoke detector 1 of the present invention is used in an explosion-proof zone. The explosion-proof zone is an area where inflammable gases that are discharged or leaked out to the atmosphere are mixed with steam and air and the concentration may be increased to such an extent that there is a danger of an explosion. The zone may sometimes be called a "hazardous region".

The preparatory step for the operation begins with attaching explosion-proofed cable glands to the side openings 44A, 44B and 44D of the enclosure 4. The labyrinth structure 2, the sensor section 3, and the enclosure 4 are then layered and the mounting screws 51A-51D are driven home into the layered. The cover 5 is further attached to the layered and the cover-mounting screws are driven home into the threaded holes. Thus a photoelectric smoke detector 1 is provided. The photoelectric smoke detector 1 may be installed with the bottom of the enclosure 4 on the ground, or with the bottom of the enclosure 4 on a wall or ceiling of facilities.

The photoelectric smoke detector 1 takes the surrounding air into the inside of the detector through an air vent 7 formed in the cover 5, shown in FIG. 1(B). The air entering the detector through the air vent 7 advances to the detecting section 23 through the shields 24 on the labyrinth structure 2 in the photoelectric smoke detector 1.

The light-emitting device 35A and the light-receiving device 35B are mounted on the upper side of the optical device mount 31 in such a manner that the detectors project from the upper side of the mount. The devices project onto the detecting section 23 of the labyrinth structure 2 of the detector 1, as shown in FIG. 5. Thus the light-emitting device 35A and the light-receiving device 35B are exposed to an explosive gas that penetrates into the detector from the air vent 7. In other words, the detectors are exposed to the explosive gas in the explosion-proof zone.

When the air penetrating into the photoelectric smoke detector 1 contains smoke, light emitted by the light-emitting device 3 is scattered by the smoke, and the pattern of light that reaches the light-receiving device 35B is changed. The change in the pattern of the received light is transmitted as an electric signal to the electronic circuit board 51 through the wiring cable 59C. Upon receiving the electric signal representing the change in the pattern of received light, the electronic circuit board 51 outputs an electric signal so as to inform the observer of the occurrence of smoke. The alarm circuit may be so designed that an output of an electric signal outputted and transmitted through the wiring cable 59D changes, for example, the color of the light emitted by the indicator light 36. This embodiment allows the observer to check whether or not smoke has occurred by observing the change in the color of the light emitted by the indicator light 36.

Figure 8:
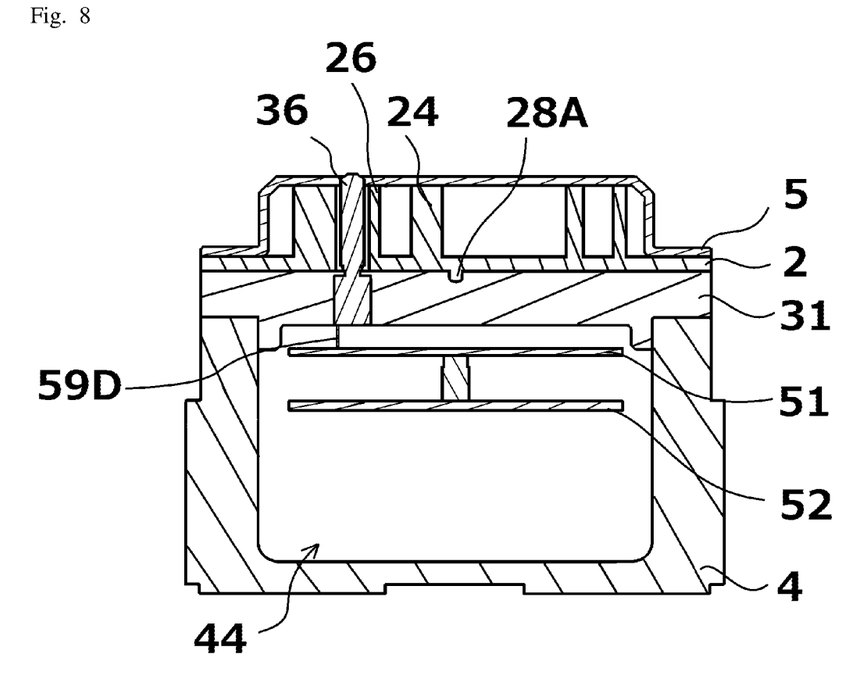
FIG. 8 is a cross-sectional view taken along line (d)-(d) in FIG. 5.
Figure 9:
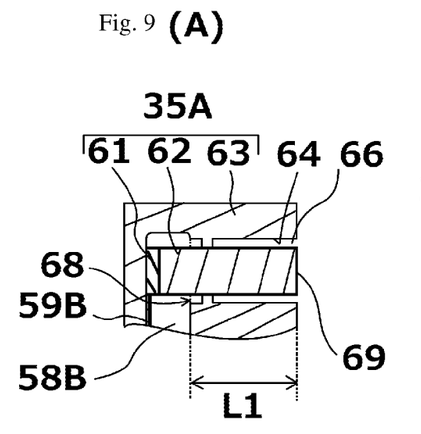
Figure 10:
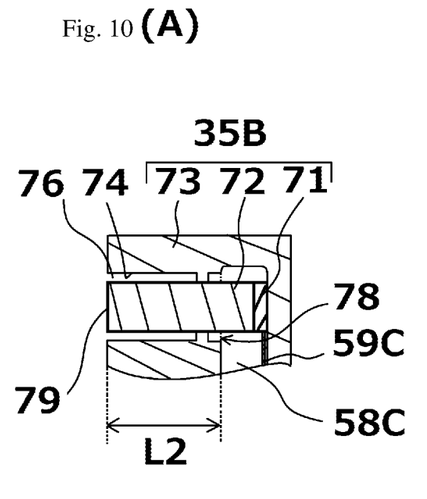

An explosive gas in the atmosphere surrounding the photoelectric smoke detector 1 may sometimes penetrate into the circuit compartment 44 through small gaps in the sealing faces 54, 55, and 56 shown in FIG. 6, the gap between the inner face A64 of the tubular wall and the outer circumferential face of the light-guiding member A62 shown in FIG. 9, the gap between the inner face B74 of the tubular wall and the outer circumferential face of the light-guiding member B72 shown in FIG. 10, and the gap between the outer circumferential face of the indicator light 36 and the inside circumferential face of the indicator light holder 26 shown in FIG. 8. The explosive gas in the circuit compartment may cause an explosion when sparks are generated on the surface of the electronic circuit board 51 by a short-circuit current or parts of the surface of the electronic circuit board 51 have an abnormally high temperature.

The enclosure 4 according to the present invention has enough strength to save itself from damage when an explosion occurs in the circuit compartment 44. Specifically, the enclosure 4 of the present invention is made of materials such as an iron plate so as not to be damaged when a pressure stipulated by the explosion-proof standards, for example a pressure of about 1.5 MPa, is applied to the enclosure by an explosion in the circuit compartment 44. Therefore flames generated by an explosion in the circuit compartment 44 do not leak to the outside of the photoelectric smoke detector 1 because of damage to the enclosure 4.

Flames generated by an explosion in the circuit compartment 44 move up toward the labyrinth structure 2 through the cavities 58B and 58C of the optical device mount 31 up to the openings A68 and B78.

Flames that have reached the opening A68 further advance toward the light-exiting end 69 of the light-guiding member A through the gap between the inner face A64 of the tubular wall and the light-guiding member A62. However, the width W1 of the gap and the length L1 of the portion of the light-guiding member A between the opening and the light-exiting end are such that the flames are extinguished while they are moving in the internal space 66. As a result, the flames are not allowed to go beyond the light-exiting end 69 of the light-guiding member A. These arrangements are capable of preventing an occurrence of serious accidents such as that where an explosive gas contained in an air that has penetrated into the detecting section 23 of the labyrinth structure 2 through the air vent 7 takes fire from flames that have moved up from the circuit compartment 44, which causes an explosion in the detecting section 23 of the labyrinth structure 2, which may lead to an explosion in the facility in which the photoelectric smoke detector is installed and further to the demolition of the entire facility. The light-receiving device 35B also has the same gap as the light-emitting device 35A has, which does not allow flames that have moved up from the circuit compartment 44 to go beyond the light-entering end 79 of the light-guiding member B as shown in FIG. 10.

More specifically, even when the photoelectric smoke detector 1 is installed in a Class-I dangerous zone where an explosive atmosphere is often created under normal conditions and the light-emitting device 35A and the light-receiving device 35B are exposed to such an atmosphere in a Class-I dangerous zone, the explosive gas surrounding the detector does not take fire from flames generated in the circuit compartment 44.

The light-emitting device 35A and the light-receiving device 35B according to the present invention do not require filling the respective peripheral spaces of the light-guiding members A62 and A72 with resin, which facilitates the production of the detector. Also, this feature contributes to the prevention of an occurrence of accidents such as that where cracks and holes are formed in the resin as a result of its deterioration over time and flames generated by an explosion leak out of the devices through the cracks and holes, which may lead to an explosion in the facility in which the photoelectric smoke detector is installed and further to the demolition of the entire facility.

Furthermore, the labyrinth structure 2 is capable of being detachably attached to the sensor section 3 provided with the light-emitting device 35A and the light-receiving device 35B. This arrangement makes it possible to easily expose the sensor section 3 to the outside just by removing the labyrinth structure 2. Therefore when the light-emitting device 35A or the light-receiving device 35B does not work normally, for example malfunctions, the operator is able to check it easily.

In addition, the labyrinth structure 2 and the sensor section 3 of the present invention are fixed to each other by engaging the first fixing part 28A of the labyrinth structure 2 with the first positioning part 38A of the sensor section 3 and by engaging the second fixing part 28B of the former with the second positioning part 38B of the latter. Thus even when an explosion occurs in the circuit compartment 44, misalignment of the labyrinth structure 2 with the sensor section 3 is prevented.

EXPLANATION OF REFERENCE SIGNS 1 photoelectric smoke detector
2 labyrinth structure 3 sensor section
4 enclosure
5 cover
7 air vent
21A-21D notch
31A-31D, 41A-41D threaded hole for fixation
22A-22D, 32A-32D threaded hole for mounting the cover
23 detecting region
24 shields
25A light-emitting device holder
25B light-receiving device holder
26 indicator light holder
26A, 27A, 27B, 36A, 36B underside opening
28A first fixing part
28B second fixing part
31 optical device mount
35A light-emitting device
35B light-receiving device
36 indicator light
38A first positioning part
38B second positioning part
42 pedestal
43 sealing portion
44 circuit compartment
44A, 44B, 44D side opening
45 tubular container
51 electronic circuit board
51A-51D mounting screw
52 protective plate
52A slit plate
52B protective cover
53 detecting area
54A, 54B, 54D plug
54, 55, 56 sealing face
57 circuit-mounting screw
58B, 58C cavity
59B, 59C, 59D wiring cable
61 light-emitting element
62 light-guiding member A
63 hollow cylindrical member A
64 inner face A of the tubular wall
66 internal space A
67, 77 light-guiding member-fixing part
68 opening A
69 light-exiting end of the light-guiding member A
71 light-receiving element
72 light-guiding member B
73 hollow cylindrical member B
74 inner face B of the tubular wall
76 internal space B
78 opening B
79 light-entering end of light-guiding member B

We claim:

1. A photoelectric smoke detector, comprising:
an explosion-proof enclosure in which a circuit compartment capable of housing an electronic circuit board is contained;
a light-emitting device; and
a light-receiving device,
wherein the light-emitting device and the light-receiving device are able to be exposed to smoke generated by an explosion,
wherein the light-emitting device comprises:
a first hollow cylindrical member having a tubular wall with a first inner face, and a first opening through which a first internal space enclosed by the first inner face of the tubular wall communicates with the circuit compartment;
a light-emitting element placed on a bottom of the first hollow cylindrical member that borders the first internal space and faces the first opening; and
a first light-guiding member for transmitting light emitted by the light-emitting element,
wherein the light-receiving device comprises:
a second hollow cylindrical member having a tubular wall with a second inner face, and a second opening through which a second internal space enclosed by the second inner face of the tubular wall communicates with the circuit compartment;
a light-receiving element placed on a bottom of the second hollow cylindrical member that borders the second internal space and faces the second opening; and
a second light-guiding member for guiding light to the light-receiving element,
wherein a gap between the first inner face and the first light-guiding member has a first width and a gap between the second inner face and the second light-guiding member has a second width,
wherein a portion of the first light-guiding member between the first opening and a light-exiting end of the first light-guiding member has a first length along an axis of the first light-guiding member and a portion of the second light-guiding member between the second opening and a light-entering end of the second light-guiding member has a second length along an axis of the second light-guiding member,
wherein the first width and the first length are arranged in such a manner that they are able to extinguish flames generated in the circuit compartment as the flames pass through the first internal space toward the light-exiting end and the second width and second length are arranged in such a manner that they are able to extinguish flames as the flames pass through the second internal space toward the light-entering end, and
wherein the gap between the first inner face and the first light-guiding member and the gap between the second inner face and the second light-guiding member each has a width of 0.1 mm or less, and the portion between the first opening and the light-exiting end of the first light-guiding member along the axis of the first light-guiding member and the portion between the second opening and the light-entering end of the second light-guiding member along the axis of the second light-guiding member each has a length of 9.5 mm or more.

2. The photoelectric smoke detector according to claim 1, wherein the photoelectric smoke detector further comprises:
an optical device mount on which the light-emitting device and the light-receiving device are mounted so as to project from a face of the mount; and
a labyrinth structure detachably layered over the mount,
wherein the labyrinth structure is provided with a light-emitting device holder and a light receiving-device holder for respectively holding the light-emitting device and the light-receiving device, and provided with shields which allows gas to pass through yet prevents light from coming from the outside to the inside, on an opposite face of a contacting face of the labyrinth structure that is layered on the face of the mount.

3. The photoelectric smoke detector according to claim 2, wherein
- the face of the optical device mount on which the labyrinth structure is layered and the contacting face of the labyrinth structure are in a shape of a circle;
- the labyrinth structure has a first fixing part on the contacting face at a center of a planform of the labyrinth structure, which planform is in a shape of a circle, and a second fixing part on the contacting face at a point in a radius of the circle, or the planform thereof;
- the optical device mount has a first positioning part in said face at a center of a planform of the optical device mount, which planform is in a shape of a circle, and a second positioning part in said face at a corresponding point in a corresponding radius of the circle, or the planform thereof, wherein the first fixing part engages with the first positioning part and the second fixing part engages with the second positioning part.

* * * * *